United States Patent [19]
Suzuki et al.

[11] Patent Number: 5,290,692
[45] Date of Patent: * Mar. 1, 1994

[54] BIOADAPTABLE POROUS CRYSTALLINE GLASS CONTAINING AN IMMOBILIZED FIBRINOLYTIC ENZYME FOR DISSOLVING BLOOD CLOTS

[75] Inventors: Takahiro Suzuki, Nagoya; Sukezo Kawamura, Inuyama; Motohiro Toriyama, Kasugai; Yoshiyuki Yokogawa; Yukari Kawamoto, both of Nagoya, all of Japan

[73] Assignee: Agency of Industrial Science & Technology, Ministry of International Trade & Industry, Tokyo, Japan

[ * ] Notice: The portion of the term of this patent subsequent to Jan. 12, 2020 has been disclaimed.

[21] Appl. No.: 852,539

[22] Filed: Mar. 17, 1992

[30] Foreign Application Priority Data

Mar. 26, 1991 [JP]  Japan ................... 3-133673

[51] Int. Cl.$^5$ ..................... C12N 11/14; A61K 37/54
[52] U.S. Cl. ................... 435/176; 424/94.63
[58] Field of Search ................. 435/176, 180; 424/94.63

[56] References Cited

U.S. PATENT DOCUMENTS 4,764,466  8/1988  Suyama et al. ............... 435/180 X
5,178,901  1/1993  Toriyama et al. ............. 427/2

FOREIGN PATENT DOCUMENTS 0482149  1/1976  Australia ................... 435/176

OTHER PUBLICATIONS

Biochim. Biophys. Acta. vol. 24 (1957), pp. 278–282, Jorgen Ploug, et al. Urokinase An Activator Of Plasminogen From Human Urine.
Agric. Biol. Chem. 55(5), pp. 1225–1232 (1991), Yasuhara Itagaki, et al. Purification & Characterization of Tissue Plasminogen Activator Secreted By Human Embryonic Lung Diploid Fibroblasts, IMR-90 Cells.
Biotechnology and Bioengineering, vol XXI pp. 461–476 (1979) John Wiley & Son's, Inc., Y. K. Cho, et al. Immobilization Of Enzymes On Activated Carbon: Selection Preparation Of The Carbon Support.
Science, vol. 166, pp. 615 to 617 (1969), Howard H. Weetall, Trypsin And Papain Covalently Coupled To Porous Glass: Preparation And Characterization.

*Primary Examiner*—David M. Naff
*Attorney, Agent, or Firm*—Oblon, Spivak, McClelland, Maier & Neustadt

[57] ABSTRACT

A fibrinolytic enzyme such as urokinase, tissue plasminogen activator or streptokinase is covalently bounded to a bioadaptable porous crystalline glass to produce a thrombolytic material. Production of the glass involves combining 40–50 mol% calcium oxide, 20–30 mol% titanium dioxide and 25–35 mol% diphosphorous pentoxide to form a mixture, and combining the mixture with 0.5–4.0 mol% disodium oxide. A bioreactor for converting plasminogen in blood into plasmin can be prepared by packing the material in a column. When finely comminuted, the material can be administered into the blood of a patient for removing blood clots.

1 Claim, No Drawings

BIOADAPTABLE POROUS CRYSTALLINE GLASS CONTAINING AN IMMOBILIZED FIBRINOLYTIC ENZYME FOR DISSOLVING BLOOD CLOTS

BACKGROUND OF THE INVENTION

1. Field of the Invention

This invention relates to a novel bioadaptable material capable of dissolving blood clots. More particularly, this invention relates to a bioadaptable material having a fibrinolytic enzyme such as urokinase or tissue plasminogen activator (hereinafter abbreviated as "TPA") immobilized on a bioadaptable porous crystallized glass. This material has the function of continuously converting plasminogen in blood into plasmin.

2. Description of the Prior Art

Blood clots are clots of blood which occur in blood vessels. When blood clots occur, they clog fine peripheral blood vessels in the human body and may cause paralysis of the hands and feet, cerebral infarct, and myocardial infarct.

The main component of blood clots is a scleroprotein called a "fibrin". This fibrin is known be decomposed by the enzyme plasmin. Plasmin is known to be present in the blood generally in the form of plasminogen, a precursor. The thrombolytic agents in popular use today include those which convert this plasminogen into plasmin and those which suppress coagulation of blood [Biochim. Biophys. Acta. Vol. 24 (1957), pp. 278–282 and Agric. Biol. Chem. 55 (5), 1,225–1,232 (1991)].

As substances which convert plasminogen into Plasmin, there can be mentioned fibrinolytic enzymes such as urokinase and TPA. Urokinase specifically acts on plasminogen, severing the alginin-valine bond thereof, and consequently converting the plasminogen into plasmin. In the past, urokinase was obtained by extraction from human urine. In recent years, however mass-production of the urokinase has been realized by the introduction of a method involving the culturing of urokinase-producing renal cells and a method of gene recombination.

TPA exhibits better ability to dissolve blood clots than urokinase because it converts plasminogen into Plasmin through union therewith and, at the same time, unites with fibrin thereby producing an environment allowing the plasmin to act easily with the fibrin. Since TPA occurs only in a very small amount in the uterus and blood vessel walls in human beings, studies have been actively pursued in search of a method for mass-production of TPA by gene recombination or cell culture. Such methods are now on the verge of being commercialized.

When a fibrinolytic enzyme such as urokinase or TPA is used as a thrombolytic agent to combat thrombosis, it is generally administered by direct injection into the patient's blood vessels. In this case, the disadvantage arises that the activity of converting plasminogen into plasmin is quickly deteriorated as by the fibrinolytic enzyme inhibiting factor in the blood and, at the same time, the plasmin activated by the fibrinolytic enzyme is quickly deprived of the thrombolytic activity by the action of the plasmin inhibiting agent in the blood.

Advances in biotechnology in recent years have led to the development of bioreactors whose elements comprise immobilized enzymes (enzymes immobilized on a carrier) and immobilized microorganisms (microorganisms immobilized on a carrier) and such bioreactors have come to be widely used in the production of useful substances, quality control in the process of production of amino acids, the analysis of foodstuffs, and clinical diagnosis.

Various methods have been proposed for the immobilization of enzymes. The carrier bonding method is one. This method accomplishes the deposition of a given enzyme by physically adsorbing the enzyme on a water-insoluble carrier [Biotechnology and Bioengineering, Vol. XXI, pp. 461 to 476 (1979), John Wiley & Sons Inc.], ion bonding and covalent bonding [Science, Vol. 166, pp. 615 to 617 (1969)]. Among these methods, the covalent bonding method is used for the broadest range of enzyme types.

As the water-insoluble carrier, inorganic porous substances are commonly used. When a fibrinolytic enzyme such as urokinase or TPA is bonded to a conventional inorganic porous substance, the porous substance may exude harmful ions through its surface or the fine surface texture of the porous substance may decay and allow the bound fibrinolytic enzyme to escape.

An object of this invention is to provide a bioadaptable material which maintains an enzymatic activity stably and efficiently for a long time and, on being administered into a patient's body of adsorbed on blood vessels, exhibits a thrombolytic activity, i.e. the function of continuously converting the plasminogen in the blood into plasmin.

SUMMARY OF THE INVENTION

The inventors continued a study with a view to developing a bioadaptable material having the properties and the thrombolytic activity just mentioned. They have consequently found that this object is accomplished by using as a carrier a porous crystallized glass produced from special raw materials and having calcium phosphate and titanium as main components thereof and immobilizing a fibrinolytic enzyme on this carrier through covalent bonding. This invention has been completed as a result.

To be specific, this invention is directed to a bioadaptable material which is produced by immobilizing through covalent bonding a fibrinolytic enzyme on a porous crystallized glass manufactured from calcium oxide, titanium dioxide, diphosphorus pentoxide, and disodium oxide and is possessed of a thrombolytic activity.

DESCRIPTION OF THE PREFERRED EMBODIMENTS

In the bioadaptable material of this invention, a bioadaptable porous crystallized glass is used as the carrier for the immobilization of the fibrinolytic enzyme. This porous crystallized glass is composed mainly of calcium phosphate and titanium and produced from calcium oxide, titanium dioxide, diphosphorus pentoxide, and disodium oxide. Specifically, it is produced by combining 100 mol parts of a mixture consisting of 45 mol% of CaO powder, 25 mol% of $TiO_2$ powder, and 30 mol% of $P_2O_5$ powder with 2 mol parts of $Na_2O$ powder, melting the resultant powder mixture at a temperature in the range of from 1,300° C. to 1,400° C., processing the resultant molten mixture in two steps, the first step at a temperature in the range of from 650° C. to 700° C. and the second step at a temperature in the range of from 730° C. to 780° C., thereby producing a crystallized glass, and immersing this crystallized glass in an aqueous solution of hydrochloric acid, nitric acid, or sulfuric acid.

The composition of the raw materials for the porous crystallized glass preferably obtained by mixing 40 to 50 mol%, 20 to 30 mol%, and 25 to 35 mol% respectively of calcium oxide, titanium dioxide, and phosphorus pentoxide and combining the resultant mixture with 0.5 to 4 mol%, based on the mixture, of disodium oxide.

The porous crystallized glass obtained from this composition exhibits highly desirable bioadaptability, possesses a large specific surface area, excels in chemical durability, and forms a strong microstructure.

There is no particular restriction on the fibrinolytic enzyme to be used in the bioadaptable material of this invention except for the requirement that it be capable of converting plasminogen into plasmin and consequently dissolving blood clots. Practical fibrinolytic enzymes include, for example, urokinase, TPA, prourokinase, and streptokinase. These enzymes may be produced naturally or obtained by such gene engineering techniques as gene recombination, cell culture or the like.

The immobilization of such a fibrinolytic enzyme through covalent bonding to the aforementioned porous crystallized glass can be carried out by any of the known methods such as, for example, the diazo method, peptide method, alkylation method, and glutaraldehyde method. Among the methods cited above, the glutaraldehyde method proves particularly desirable.

The amount of the enzyme immobilized on the carrier is preferably in the range of from 1 to 10 mg as dry material per 1 g of the carrier.

The bioadaptable material of this invention obtained as described above and consequently having thrombolytic activity retains the activity stably and effectively for a long time. This material as packed in a column can be used as a bioreactor to be operated by introducing blood therein, thereby effecting continuous conversion of plasminogen in the blood into plasmin. Such a bioreactor can be expected to find utility as an apparatus for combating thrombosis.

When the bioadaptable material of this invention possessed of the thrombolytic activity is finely comminuted and administered into the blood of a patient, it can be utilized as an in vivo cure material for producing a long-term thrombolytic action and decomposing and removing blood clots or precursors thereof.

The enzyme-porous crystallized glass composite material obtained by the method of this invention contains no harmful substance to the living system and possesses a microstructure excellent in durability and, therefore, can be expected to find utility in numerous applications in medicine and food production processes.

The bioadaptable material of this invention possessed of thrombolytic ability is a product obtained by immobilizing a fibrinolytic enzyme such as urokinase or TPA on a porous crystallized glass having calcium Phosphate and titanium as main components thereof. It is, therefore, excellent in bioadaptability and capable of continuously converting plasminogen in blood into plasmin. Thus, it can be advantageously used as a thrombolytic material.

This invention will now be described more specifically below with reference to working examples. It should be noted that this invention is not limited in any sense to or by these examples.

EXAMPLE 1

A mixture consisting of 45 mol% of CaO powder, 25 mol% of $TiO_2$ powder, and 30 mol% of $P_2O_5$ powder was combined with 1 to 3 mol% of $Na_2O$ powder. The resultant mixed powder was melted at 1,350° C. and then processed in two steps, the first step at 670° C. and the second step at 750° C., to produce a crystallized glass. Then, this crystallized glass was immersed in hydrochloric acid having a concentration of 3% by weight, to produce a porous crystallized glass. When this porous crystallized glass was tested for bioadaptability in tissue cell culture using cells originating in the human fetal kidney, it exhibited highly satisfactory bioadaptability.

Then, a urokinase-porous crystallized glass composite, i.e. a bioadaptable material of this invention, was produced by immobilizing urokinase through covalent bonding by the glutaraldehyde method on the porous crystallized glass. When this composite was packed in a column and an artificial vital fluid containing 1% by weight of serum was continuously supplied to the column, the plasmin activity in the eluate remained at a high level for more than 10 hours.

EXAMPLE 2

When the procedure of Example 1 was faithfully repeated, except that an artificial vital fluid containing 10% by weight of serum was used in the place of the artificial vital fluid containing 10% by weight of serum, the plasmin activity in the eluate remained at a high level for more than 1 hour.

COMPARATIVE EXPERIMENT 1

When the procedure of Example 1 was repeated faithfully, except that a $3Al_2O_3\text{-}2SiO_2$ type ceramic porous material was used in the place of the porous crystallized glass, the test for bioadaptability with cells from human fetal kidney showed a decline of about 20% in terms of speed of growth. The plasmin activity in the eluate was about 40% lower than that obtained through the column using the porous crystallized glass.

COMPARATIVE EXPERIMENT 2

When the procedure of Example 1 was faithfully repeated, except that a $SiO_2$ type porous glass was used in the place of the porous crystallized glass, the test for adaptability with cells from a human fetal kidney showed a fall of about 10% in terms of the speed of growth. The plasmin activity in the eluate sharply fell as compared with that using the porous crystallized glass.

What is claimed is:

1. A thrombolytic bioadaptable material comprising:
   a bioadaptable porous crystalline glass produced by combining 40-50 mol% calcium oxide, 20-30 mol% titanium dioxide, and 25-35 mol% diphosphorous pentoxide to form a mixture, and combining said mixture with 0.5 to 4.0 mol%, based on said mixture, of disodium oxide; and
   at least one fibrinolytic enzyme capable of converting plasminogen into plasmin selected from the group consisting of urokinase, tissue plasminogen activator, and streptokinase covalently bonded to said porous crystalline glass, whereby said at leas tone fibrinolytic enzyme is immobilized on said porous crystalline glass.

* * * * *